United States Patent
Biggs

(10) Patent No.: US 7,343,827 B2
(45) Date of Patent: Mar. 18, 2008

(54) SYSTEM AND PROCESS FOR BREAK DETECTION IN POROUS ELEMENTS FOR SCREENING OR FILTERING

(75) Inventor: Michael A. Biggs, Maineville, OH (US)

(73) Assignee: M-I L.L.C., Houston, TX (US)

( * ) Notice: Subject to any disclaimer, the term of this patent is extended or adjusted under 35 U.S.C. 154(b) by 289 days.

(21) Appl. No.: 11/270,050

(22) Filed: Nov. 8, 2005

(65) Prior Publication Data
US 2007/0101802 A1  May 10, 2007

(51) Int. Cl.
G01M 19/00 (2006.01)
B07B 1/28 (2006.01)

(52) U.S. Cl. ........... 73/865.8; 209/346; 209/359; 209/360

(58) Field of Classification Search ........... 73/865.8; 209/309, 310, 325, 346, 359, 360; 324/96
See application file for complete search history.

(56) References Cited

U.S. PATENT DOCUMENTS

| | | | |
|---|---|---|---|
| 4,995,259 A * | 2/1991 | Khuri-Yakub et al. | 73/593 |
| RE34,731 E * | 9/1994 | Lee et al. | 73/304 C |
| 5,351,543 A * | 10/1994 | Migliori et al. | 73/579 |
| 5,384,543 A * | 1/1995 | Bible et al. | 324/644 |
| 5,602,474 A * | 2/1997 | Morrey, Jr. | 324/238 |
| 5,950,841 A * | 9/1999 | Knox et al. | 209/315 |
| 6,501,414 B2 * | 12/2002 | Arndt et al. | 342/22 |
| 6,953,121 B2 * | 10/2005 | Olsen et al. | 209/309 |
| 6,989,675 B2 * | 1/2006 | Kesil et al. | 324/636 |
| 6,997,325 B2 * | 2/2006 | DeCenso | 209/401 |
| 7,182,207 B2 * | 2/2007 | DeCenso | 209/401 |
| 2003/0193331 A1 * | 10/2003 | Nath et al. | 324/240 |
| 2003/0205088 A1 * | 11/2003 | Passarelli, Jr. | 73/643 |
| 2004/0134280 A1 * | 7/2004 | Hedberg et al. | 73/579 |
| 2005/0247603 A1 * | 11/2005 | DeCenso et al. | 209/235 |

FOREIGN PATENT DOCUMENTS

| | | | |
|---|---|---|---|
| JP | 03199961 A | * | 8/1991 |
| JP | 10206396 A | * | 8/1998 |
| WO | WO 2004045198 A2 | * | 5/2004 |

* cited by examiner

*Primary Examiner*—Daniel S. Larkin
*Assistant Examiner*—David A. Rogers
(74) *Attorney, Agent, or Firm*—Connolly Bove Lodge & Hutz LLP

(57) ABSTRACT

A method of detecting breaks in a porous element in a material separator is disclosed. A shielding is created in the material separator to form a barrier to RF energy. The shielding is formed with a path through the barrier capable of allowing RF energy and material to flow therethrough. The electrically conductive porous element is positioned fully across the path. An RF signal is transmitted on one side of the porous element, and signal levels of the RF signal are detected on the other side of the porous element, such that the detected RF signal crosses the porous element. A baseline signal strength indicator is established from the detected signal levels using an unbroken porous element. An operative signal strength indicator is generated from the detected signal levels. Breaks in the porous element are detected by comparing the operative signal strength indicator against the baseline signal strength indicator.

15 Claims, 3 Drawing Sheets

SYSTEM AND PROCESS FOR BREAK DETECTION IN POROUS ELEMENTS FOR SCREENING OR FILTERING

BACKGROUND OF THE INVENTION

1. Field of the Invention

The field of the present invention is material separation through screening or filtering and break detection for the porous elements employed.

2. Background

Separator systems are used in industry for a variety of undertakings. They are used to process dry materials and liquid/solid slurries. Each one typically functions by first introducing a flow of material to a porous element such as a screen or filter, usually of woven wire mesh or a porous membrane. The flow of material is separated into two streams, one containing material that passes through the porous element, the other containing material that is rejected by the porous element. A drive mechanism may be operatively coupled with a housing to produce a vibrating motion that serves to put the material on the porous element in motion until it either passes through or is pushed off the element at the periphery thereof. Other devices use pressure to increase flow through a membrane with cycled application including reverse flow to clear the rejected material.

Such separator systems employ screens in rectangular and circular forms with screen elements tensioned on frames or with hooks tensioned on the separator itself. The screen elements range greatly in porosity and can be of a single element or of laminated elements. The separator frames can be vibratory or fixed and, when vibratory, supported by a variety of means such as springs, bushings or links. Such systems alternatively employ filters, tensioned or untensioned, supported or unsupported and of widely varying porosities and shapes including rectangular, circular, cylindrical and bag shaped. Many additional features are, of course, available such as housing covers, elaborate manifolds and various and changeable motions, rates and cycles. Patents disclosing a small sampling of such systems and components include U.S. Pat. No. 4,022,693; U.S. Pat. No. 4,251,354; U.S. Pat. No. 4,582,597; U.S. Pat. No. 4,613,432; U.S. Pat. No. 4,655,911; U.S. Pat. No. 4,968,366; U.S. Pat. No. 5,032,210; U.S. Pat. No. 5,051,171; U.S. Pat. No. 5,134,893; U.S. Pat. No. 5,221,008; U.S. Pat. No. 5,226,546; U.S. Pat. No. 5,242,058; U.S. Pat. No. 5,255,789; U.S. Pat. No. 5,265,730; U.S. Pat. No. 5,271,504; U.S. Pat. No. 5,456,365; U.S. Pat. No. 5,950,841; U.S. Pat. No. 6,089,380; U.S. Pat. No. 6,202,856; U.S. Pat. No. 6,349,834; U.S. Pat. No. 6,431,368; and U.S. Pat. No. 6,513,665, the disclosures of which are incorporated herein by reference.

Materials typically screened vary considerably in their particle size, bulk density, chemical composition, temperature, moisture content and other physical and chemical characteristics. Any particular separator system in a given processing plant is likely dedicated to handling a single material with consistent properties. Examples of such materials, to show the diversity but not to provide a comprehensive list, include:

| | |
|---|---|
| abrasives | activated carbon |
| calcium carbonates | ceramic slurries |
| chlorine compounds | citric acid |
| fertilizers | flours |
| food products | gunpowder |
| minerals | paper coating slurries |
| pharmaceuticals | pigments |
| polystyrene beads | powdered metals |
| powdered paints | printing inks |
| PVC powder | refractories |
| rocket propellants | starches |

As a result, various screen configurations, vibration profiles and environments are employed to maximize efficiency and the quality of the resulting processed materials.

By far the most common failure mode for separator systems is the failure of the porous element. Screens, for example, are typically made of finely woven wire cloth drawn taut by a screen frame or tensioning apparatus on the separator. Failure is caused by numerous factors such as wear and fatigue failure. Such failures typically occur as breaks in the screening media itself resulting in a damaged screen. Such breaks may manifest themselves as tears (a series of mutually adjacent broken wires), punctures (tears in two directions) or holes (missing portions of the screening material). Once the screen has failed, the function of a separating system is compromised. At a minimum, it can no longer be relied upon to reject all oversized material because such material can now pass through the break in the screen. Worse, it can result in fragments of the failed screen contaminating the material being screened, presenting a serious hazard in food or pharmaceutical screening operations. Similar failure occur in filter elements.

As the porous elements are typically located within closed housings or under material being processed, it is difficult to visually detect such failures. Thus, where critical separation is demanded, frequent inspection is advisable. As such efforts to insure quality separation result in downtime and labor and still result in compromised processed material, methods for detecting breaks have been long sought. Systems have been devised that attempt to detect screen failure by measuring the electrical or optical paths through the mesh screen itself. See U.S. Pat. No. 5,996,807, the disclosure of which is incorporated herein by reference. These are believed to have been proven impractical and have not met with general market acceptance.

SUMMARY OF THE INVENTION

The present invention is directed toward a method of detecting breaks in porous elements for separator systems. An RF signal is transmitted from one side of a porous element mount and detected on the other side of the porous element. Breakage which results in holes large enough to let additional amounts of RF signal pass through the porous element is an indication that the porous element has failed.

In a first separate aspect of the present invention, the RF signal is in the microwave range of electromagnetic energy. Transmission of the RF signal is performed by sweeping the RF signal through a plurality of discrete frequencies.

In a second separate aspect of the present invention, signal levels of the RF signal are detected at a plurality of distinct frequencies. These signal levels are used to establish a baseline signal strength indicator using an unbroken porous element. The signal levels are then used to monitor the porous element for failure. The detected signal levels are used to generate a operative signal strength indicator. The operative signal strength indicator is then compared against the baseline signal strength indicator to detect a break in the porous element. Preferably, both the baseline signal strength indicator and the operative signal strength indicator are formed by averaging two or more detected signal levels, and more preferably by averaging the three highest detected signal levels from among the plurality of discrete frequencies.

In a third separate aspect of the present invention, any of the foregoing aspects may be employed in combination.

Accordingly, an improved method of detecting breaks in the porous elements of material separators is disclosed. Other objects and advantages will appear hereinafter.

BRIEF DESCRIPTION OF THE DRAWINGS

In the drawings, wherein like reference numerals refer to similar components.

DETAILED DESCRIPTION OF THE PREFERRED EMBODIMENTS

Figure 1:
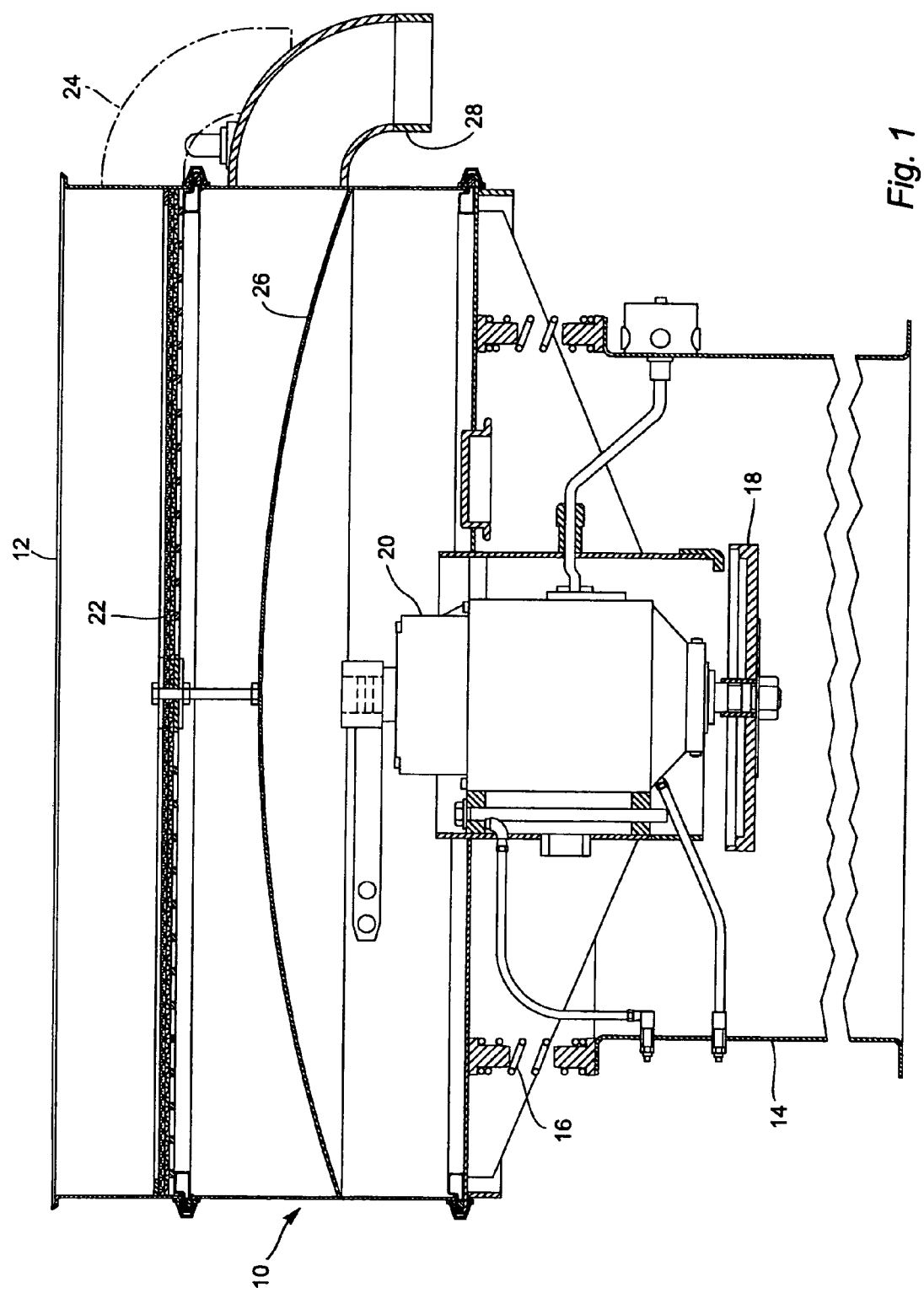
FIG. 1 is a cross-sectional view of a vibratory material separator with which a detector may be employed.

Turning in detail to the drawings, FIG. 1 illustrates a conventional vibratory screen material separator, generally designated 10, to provide context for one material separation system for detecting breaks in a porous element. Nonvibratory screening systems and filtration systems in a range of such systems described above in the Background of the Invention can also find increased utility with a system for detecting breaks in the porous element employed for material separation.

The separator 10 includes a housing 12 which is elastically mounted to a base 14 on springs 16. A vibration generator 18 driven by a motor 20 causes the elastically mounted housing 12 to vibrate at an advantageous frequency and amplitude for material screening or filtering. A porous element, which is a screen 22 in this embodiment, extends across the housing 12 to separate material deposited thereon by selected characteristics. Above the screen 22 is an overs outlet 24 while below the screen 22 is a domed manifold 26 which feeds a throughs outlet 28.

Figure 3:
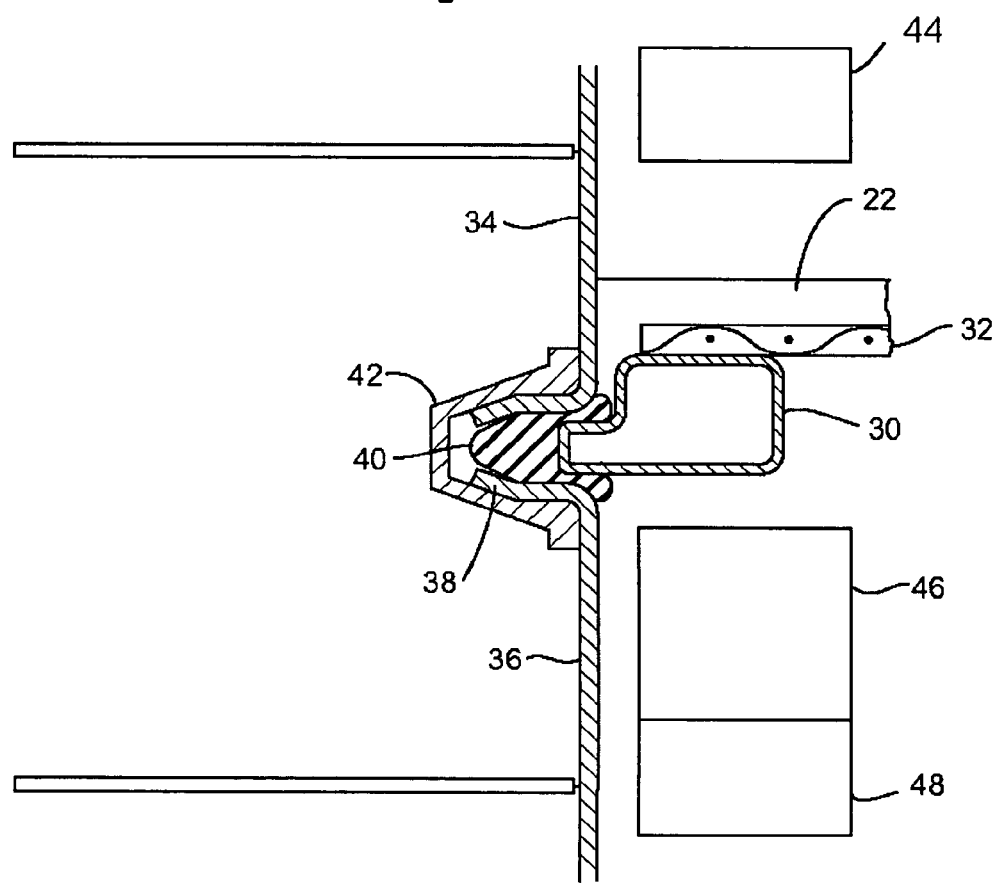
FIG. 3 is a housing seal arrangement associated with the devices of FIGS. 1 and 2.

Referring to FIG. 3, the seal arrangement and construction of the housing 12 about the screen 22 is illustrated. Also illustrated are details of the porous element, defined in this embodiment as a screen 22. The screen 22 includes a screen frame 30 which may be a formed metal ring. Screen cloth 32 is bonded to the screen frame 30 in a taut state. The screen cloth 32 is typically wire mesh of electrically conductive stainless steel. Preconfigured interstices are defined by the weave, the wire diameter, and the wires per unit measure.

The housing 12 is formed of two cylindrical housing elements 34 and 36. These elements 34 and 36 come together about a flange 38 on the screen frame 30. As such, a screen mount is defined therebetween fully about the interior of the housing 12. A gasket 40 is positioned about the flange 38 and a clamp band 42 draws the entire assembly together. The entire separator 10 also is contemplated to include a cover with an inlet therein through which material is delivered to the screen 22.

In creating a chamber within the housing 12 which includes a barrier to an RF signal, the housing components 34 and 36 are electrically conductive. The cover (not shown) might also be electrically conductive as well as the domed manifold 26 beneath the screen 22. The overs outlet 24 and the throughs outlet 28 can also be electrically conductive and further electrically conductive shielding as may be needed is contemplated to prevent transmission of the RF signals therethrough. Further, the gasket 40 is anticipated to be electrically conductive or to require an electrically conductive barrier to prevent the RF signals from flowing around the screen frame 30 within the screen mount. The conductivity is provided through the employment of sheet metal components acting to create a barrier to the RF signals.

With the aforementioned components, the housing 12 may define a chamber having a barrier to the RF signals either above or below the screen 22. Below the screen 22, the housing element 36, the domed manifold 26, the throughs outlet 28 and the gasket 40, along with other shielding as may be required, define a first chamber. The upper housing element 34, the overs outlet 24, the gasket 40 and a cover (not shown), again with additional shielding as may be needed, may define a second chamber with a barrier to the RF signals.

Between these two defined spaces, whether both form a chamber or only one forms a chamber with an RF barrier, a path exists through the screen mount. Without the screen 22, material to be processed has a clear path. So do the RF signals. The screen 22, positioned across this path in the screen mount defined by the housing 12 creates a selective path for material being processed according to selected characteristics. By selecting the appropriate RF signal, the screen 22 of conductive metal wire can act as a barrier to substantially attenuate, including to the point of virtual elimination, the RF signal passage along the path across the screen 22 so long as the preconfigured interstices of the unbroken screen remain intact. The screen 22 having interstices in the range of commercial screening systems is a barrier to RF signals in the microwave range. Other porous elements including screens and membranes which block microwaves in addition to woven wire screen cloth can be employed. As one example, electrically conductive coating on nonconductive substrates may adequately block RF signals in the appropriate range.

In the preferred embodiment, the porous element defined by the screen 22, which embodies a barrier across the path to the chamber, is shown to extend in a plane. Instead, the porous element may extend into or out from the main volume of a defined chamber as a filter bag or a cylinder, for example, and the path may, therefore, not necessarily be linear but passes through a porous element mount with the porous element extending fully across the path. The frame retaining the edges of the porous element may be fixed to the porous element as with the screen 22 or may be a mechanism with the housing, thus becoming part of the porous element mount.

Figure 2:
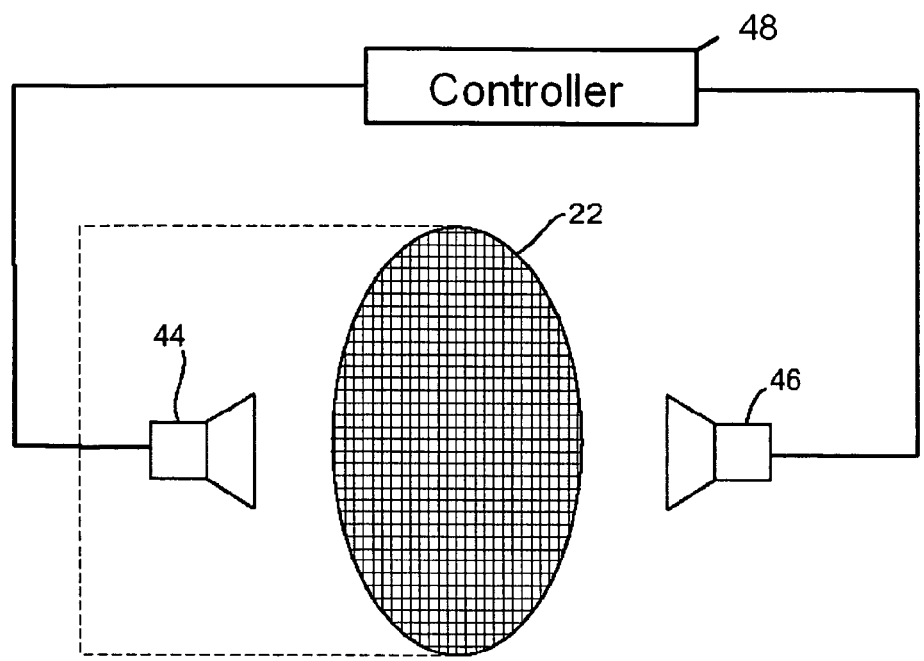
FIG. 2 is a schematic view of a detector as associated with the separator of FIG. 1.

A break detection system, illustrated in FIG. 2 schematically, is employed with the vibratory material separator 10 as part of the separator system. The break detection system includes an RF transmitter 44, an RF receiver 46, each located on opposite sides of the screen 22, and a controller 48 which controls both the transmitter 44 and the receiver 46. The transmitter 44 and the receiver 46 may be mounted to or relative to the housing components 34 and 36, respectively. The break detection system and the components thereof operate in the RF (radio frequency) range and, more practically given the size of the preconfigured interstices of commercial screens 22, operate at the higher end of the RF range in the microwave range, with the break detection system, the transmitter 44 and the receiver 46 being microwave elements. The RF signals are understood to fall in the range of 700 MHz to 50 GHz with specific empirical tuning to match the characteristics of the screen 22 employed. For purposes of compliance with U.S. government RF emission regulations, the transmitter 44 preferably transmits signals within the 5.725 GHz to 5.875 GHz region. Other appropriate frequency ranges, however, may be employed as desired, such as near the 900 MHz band, the 2.4 GHz band, the 10 GHz band, and the 24 GHz band, among others.

The controller 48, which may include a microprocessor, manages operation of the transmitter 44 and the receiver 46 and determines whether the screen 22 has failed (i.e., the screen 22 has a rip, tear, puncture, or the like). The controller 48 detects changes in the physical state of the screen 22 when a break occurs and generates a signal as may be desired by the operator, such as sounding an audible alarm, providing a visual indicator, cutting power to the separator, providing an electronic output for customization, and the like.

In the preferred embodiment, the transmitter 44 is operated to sweep through a series of discrete frequencies. The transmitter 44 starts at or near 5.73 GHz and repeatedly sweeps or steps through 20 discrete frequencies in 5 MHz increments. Likewise, the receiver 46 is operated to detect signal levels at the emitted frequencies as the transmitter 44 sweeps through the frequency range. The signal levels detected by the receiver are communicated to the controller for further processing to determine whether the screen 22 has failed. Of course, the frequency at which the sweeps begin and the increments between each step is a matter of design choice and will typically depend upon the particular implementation.

During set-up of the system (i.e., any installation of a new screen 22 into the separator 10), a baseline signal strength indicator is established using an unbroken screen 22. The controller 48 uses the baseline signal strength indicator to determine whether a break has formed in the screen 22. The preferred method for establishing the baseline signal strength indicator is to sweep the transmitter 44 through the series of discrete frequencies, measure a signal level at each discrete frequency, analyze the signal levels to identify the three highest signal levels (or "peaks") among all of those signal levels measured in one sweep, then average the three highest signal levels to arrive at the baseline signal strength indicator. In practice, any number of signal level peaks may be used to establish the baseline signal strength indicator. However, use of the three highest peaks has been empirically established to be sufficient for break detection.

After the baseline signal strength indicator is established, the system monitors the screen 22 for breaks. The receiver 46 continues to communicate detected signal levels to the controller 48, and the controller 48 uses those detected signal levels to generate the operative signal strength indicator, which is generated using the same averaging technique described above for the baseline signal strength indicator.

When the integrity of the barrier defined by the porous element, in this case the screen 22, fails in any manner which increases an opening size, the size of the resulting opening enables transmission of the RF signal through that opening. This directly results in an increase in signal levels at the detector 48. Experiments have shown that detection is likely with the opening achieving one-quarter the wavelength. Therefore, a comparison of the operative signal strength indicator with the baseline signal strength indicator provides an indication of whether or not the porous element has failed.

Figure 4:
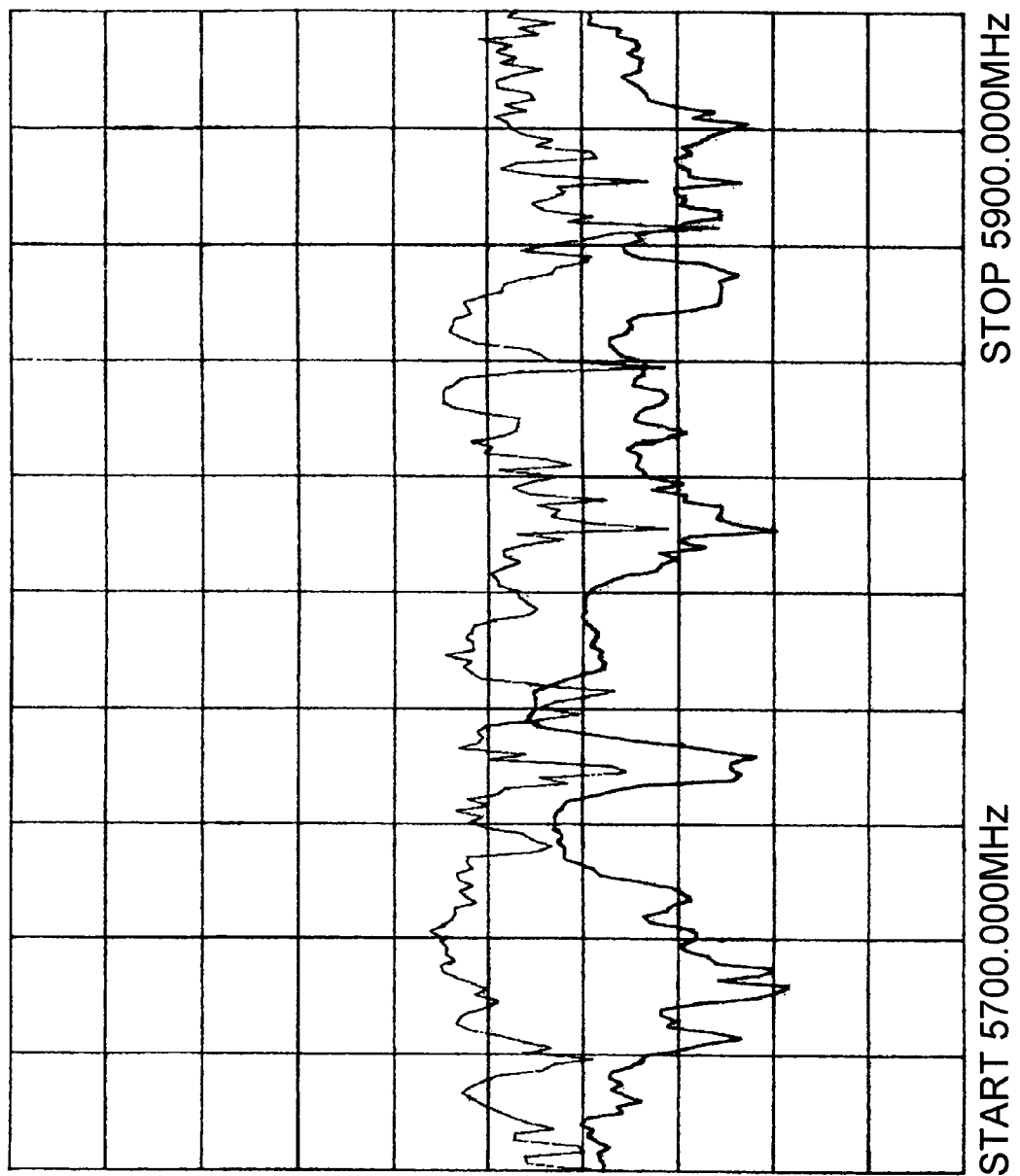
FIG. 4 is a graphic illustration of a comparison between signal levels from an unbroken porous element and those from a failed porous element.

FIG. 4 is a graphic illustration of signal levels which result from two continuous sweeps between 5.7 GHz and 5.9 GHz. This graph emphasizes how the system may use any frequency range and any frequency step increments within the chosen range in order to detect screen failures. The first signal level sweep 50 is from an intact screen, while the second signal level sweep 52 is from a torn screen. It is notable that at several frequencies within this range the signal level from the intact screen is greater than the signal level from the torn screen. This is generally due to the presence of standing waves at that frequency. Obviously, if the system only measured the signal level at a single frequency, it is entirely possible that a tear in the screen would not be detected. On the other hand, the average of the three highest peaks for each sweep may be taken to avoid this problem, regardless of the overall range of the frequency sweep and whether the sweep is continuous or performed as a series of discrete steps. The signal level sweep 50 for the intact screen has the three highest peaks circled and labeled as A, B, and C. The signal level sweep 52 for the torn screen has the three highest peaks circled and labeled as A', B', and C'. It is self-evident from the graph of FIG. 4 that the average of the signal levels at A', B', and C' is greater than the average of the signal levels at A, B, and C.

In operation the process for detecting breaks during processing of material through the material separator 10 includes the transmission of an RF signal most appropriately in the microwave range and tuned to the RF barrier characteristics of the porous element, the screen 22 in this embodiment, on the first side thereof. The transmitter 44 operates at a frequency with a wave length that is longer than the preconfigured interstices in the screen 22 such that an intact screen will significantly attenuate the signal. Such a differential may be an order of magnitude. With the screen 22 intact, the receiver 46 can be used to define the base line signal transmission characteristics to establish an appropriate threshold. Once a failure has occurred in the screen 22, the resulting enlarged opening will reduce the screen's attenuation of the microwave signal. This allows a stronger signal to reach the receiver 46. Through the use of either analog or digital signal processing techniques, this difference in signal strength is detected and appropriate alarms activated so that the screening process operator can take corrective action.

Preferably, the microwave system operates continuously and is able to announce a fault as soon as it occurs. While this is preferred, it is not always necessary given that in most processing operations immediate corrective action (such as stopping the line) is not possible. The system can be put to effective use in an intermittent monitoring mode such that it identifies the occurrence of a screen failure within a relative short period of time after its actual occurrence. This time value will vary by industry, but a matter of minutes is sufficient for practically all applications.

Preferably, measurements are made while the separator 10 is operating. In doing so, the microwave system and the screen 22 that is being monitored will be subjected, in conventional equipment, to a magnitude of approximately 2 to 4 G's at a frequency of 4 to 30 Hz. depending on the separator used. Alternatively, the separator 10 could be stopped briefly while a measurement is taken.

It is also preferred that measurements be made while the separator 10 is processing material. While doing so, the screen 22 may be covered with material to various depths. With most materials, the RF signal will be able to pass through these depths and not be affected to the point that the signal will not be effective. With problematic materials, inflow to the separator 10 may be turned off while the separator 10 continues to operate. In this way, the processed material is flushed out before a measurement is taken.

In setting up the system, shielding is undertaken. Inherently, separators 10 provide a substantial amount of shielding as they are constructed almost entirely of electrically conductive material such as stainless steel alloys. Sealing about the screen 22 is conventional. However, the seals 40 are typically elastomeric. Further, the ports associated with the overs outlet 24 and throughs outlet 28 provide electrically conductive paths, along with the elastomeric seals 40, for circumventing the path through the screen 22. Electrically conductive material molded into gasket and discharge components, replacement of such components by electrically conductive devices or shielding around these devices themselves can provide adequate signal attenuation such that the receiver 46 can distinguish between screens 22 which are intact and those which have experienced a significant break. Depending on the materials processed, additional events may be sensed such as screen blinding.

Thus, a screening or filtering system capable of detecting breaks is disclosed. While embodiments and applications of this invention have been shown and described, it would be apparent to those skilled in the art that many more modifications are possible without departing from the inventive concepts herein. The invention, therefore is not to be restricted except in the spirit of the appended claims.

What is claimed is:

1. A method of detecting breaks in a porous element in a material separator, the method comprising:
    creating shielding in the material separator forming a barrier to radio frequency (RF) energy with a path through the barrier capable of allowing RF energy and material to flow therethrough;
    positioning the porous element fully across the path, wherein the porous element is electrically conductive;
    providing an RF transmitter on one side of the porous element and an RF receiver on the other side of the porous element;
    operating the transmitter to sweep an RF signal through a range of frequencies;
    operating the receiver to detect the signal level at a plurality of discrete frequencies within the range of frequencies and using a controller to determine an operative signal strength from the received signals; and
    determining that a break in the porous element is present by comparing the operative signal strength to a baseline signal strength indicator for the porous element,
    wherein the baseline signal strength indicator for the porous element is determined when the porous element is unbroken by operating the transmitter to sweep an RF signal through a range of frequencies, operating the receiver to detect the signal level at a plurality of discrete frequencies within the range of frequencies wherein the detected RF signals cross the unbroken porous element, and establishing the baseline signal strength indicator from the detected signal levels.

2. The method of claim 1, wherein transmitting the RF signal includes sweeping the transmitted RF signal through the plurality of discrete frequencies.

3. The method of claim 1, wherein the electrically conductive porous element comprises a screen including metal screen cloth.

4. The method of claim 1, wherein establishing the baseline signal strength indicator includes averaging two or more detected signal levels.

5. The method of claim 4, wherein establishing the baseline signal strength indicator includes averaging the three highest detected signal levels.

6. The method of claim 1, wherein generating the operative signal strength indicator includes averaging two or more detected signal levels.

7. The method of claim 6, wherein generating the operative signal strength indicator includes averaging the three highest detected signal levels.

8. A method of detecting breaks in a porous element in a material separator, the method comprising:
    creating shielding in the material separator forming a barrier to radio frequency (RF) energy with a path through the barrier capable of allowing RF energy and material to flow therethrough;
    positioning the porous element fully across the path, wherein the porous element is electrically conductive;
    providing an RF transmitter on one side of the porous element and an RF receiver on the other side of the porous element;
    operating the transmitter to sweep an RF signal through a range of frequencies in the microwave range of electromagnetic energy;
    operating the receiver to detect the signal level at a plurality of discrete frequencies within the range of frequencies and using a controller to determine an operative signal strength from the received signals; and
    determining that a break in the porous element is present by comparing the operative signal strength to a baseline signal strength indicator for the porous element,
    wherein the baseline signal strength indicator for the porous element is determined when the porous element is unbroken by operating the transmitter to sweep an RF signal through a range of frequencies, operating the receiver to detect the signal level at a plurality of discrete frequencies within the range of frequencies wherein the detected RF signals cross the unbroken porous element, and establishing the baseline signal strength indicator from the detected signal levels.

9. The method of claim 8, wherein the electrically conductive porous element comprises a screen including metal screen cloth.

10. The method of claim 9, wherein establishing the baseline signal strength indicator includes averaging two or more detected signal levels.

11. The method of claim 10, wherein establishing the baseline signal strength indicator includes averaging the three highest detected signal levels.

12. The method of claim 9, wherein generating the operative signal strength indicator includes averaging two or more detected signal levels.

13. The method of claim 12, wherein generating the operative signal strength indicator includes averaging the three highest detected signal levels.

14. A method of detecting breaks in a porous element in a material separator, the method comprising:
    creating shielding in the material separator forming a barrier to radio frequency (RF) energy with a path through the barrier capable of allowing RF energy and material to flow therethrough;
    positioning the porous element fully across the path, wherein the porous element is electrically conductive;

providing an RF transmitter on one side of the porous element and an RF receiver on the other side of the porous element;

operating the transmitter to sweep an RF signal through a series of discrete frequencies in the microwave range of electromagnetic energy;

operating the receiver to detect the signal level at each discrete frequency and using a controller to determine an operative signal strength from the received signals by averaging two or more detected signal levels; and determining that a break in the porous element is present by comparing the operative signal strength to a baseline signal strength indicator for the porous element, wherein the baseline signal strength indicator for the porous element is determined when the porous element is unbroken by operating the transmitter to sweep an RF signal through a series of discrete frequencies, operating the receiver to detect the signal level at each discrete frequency wherein the detected RF signals cross the unbroken porous element, and establishing the baseline signal strength indicator from the detected signal levels by averaging two or more detected signal levels.

15. The method of claim 14, wherein the electrically conductive porous element comprises a screen including metal screen cloth.

* * * * *